United States Patent
Yoshida et al.

(10) Patent No.: US 7,754,939 B2
(45) Date of Patent: Jul. 13, 2010

(54) DISPOSABLE DIAPER HAVING ANTISLIP ELEMENTS

(75) Inventors: Masaki Yoshida, Kagawa-ken (JP); Hironao Minato, Kagawa-ken (JP); Koichiro Mitsui, Kagawa-ken (JP)

(73) Assignee: Uni-Charm Corporation (JP)

( * ) Notice: Subject to any disclaimer, the term of this patent is extended or adjusted under 35 U.S.C. 154(b) by 518 days.

(21) Appl. No.: 11/462,190

(22) Filed: Aug. 3, 2006

(65) Prior Publication Data

US 2006/0264862 A1 Nov. 23, 2006

Related U.S. Application Data

(62) Division of application No. 10/870,470, filed on Jun. 18, 2004, now Pat. No. 7,150,732.

(30) Foreign Application Priority Data

Jun. 20, 2003 (JP) .............................. 2003-176236

(51) Int. Cl.
 *A61F 13/15* (2006.01)
 *A61F 13/20* (2006.01)
(52) U.S. Cl. .................................... 604/367
(58) Field of Classification Search ............ 604/385.01, 604/385.24–385.28, 386, 389
 See application file for complete search history.

(56) References Cited

U.S. PATENT DOCUMENTS

| 4,381,781 | A | 5/1983 | Sciaraffa et al. |
| 5,370,634 | A | 12/1994 | Ando et al. |
| 5,782,819 | A | 7/1998 | Tanzer et al. |
| 5,858,013 | A | 1/1999 | King |
| 6,213,991 | B1 * | 4/2001 | Kling et al. ............ 604/385.01 |
| 6,287,287 | B1 * | 9/2001 | Elsberg .................. 604/385.03 |
| 6,391,438 | B1 * | 5/2002 | Ramesh et al. ........... 428/319.7 |
| 6,478,784 | B1 | 11/2002 | Johnson et al. |
| 6,626,879 | B1 | 9/2003 | Ashton et al. |
| 6,746,433 | B1 | 6/2004 | Shimoe et al. |
| 6,918,900 | B2 | 7/2005 | Johnson |
| 2003/0055394 | A1 | 3/2003 | Gibbs |
| 2003/0135185 | A1 | 7/2003 | Crowther |

FOREIGN PATENT DOCUMENTS

| JP | 10-309299 | 11/1998 |
| WO | WO 9813002 A1 * | 4/1998 |

* cited by examiner

*Primary Examiner*—Melanie J Hand
(74) *Attorney, Agent, or Firm*—Lowe Hauptman Ham & Berner, LLP

(57) ABSTRACT

A disposable diaper includes antislip elements having a frictional force higher than those of end flaps and side flaps. These antislip elements are attached to portions of the end flap extending immediately outside transversely opposite ends of a waist elastic member on the side of these portions facing away from the diaper wearer's skin. The waist elastic member is, in turn, attached to the end flap.

13 Claims, 17 Drawing Sheets

DISPOSABLE DIAPER HAVING ANTISLIP ELEMENTS

RELATED APPLICATIONS

The present application is a divisional application of U.S. patent application Ser. No. 10/870,470, filed Jun. 18, 2004, which is based on, and claims priority from, Japanese Application Serial Number 2003-176236, filed Jun. 20, 2003, the disclosure of which is hereby incorporated by reference herein in its entirety.

BACKGROUND OF THE INVENTION

The present invention relates to a disposable diaper for absorption and containment of body discharges.

A disposable diaper is well known in the art, which defines, in a longitudinal direction, front and rear waist regions and a crotch region extending between these waist regions and having a body fluid absorbing zone extending over the crotch region further into the front and rear waist region, a pair of end flaps extending in a transverse direction outside longitudinally opposite ends of the absorbing zone, a pair of side flaps extending in a longitudinal direction outside transversely opposite side edges of the absorbing zone, a pair of tape fasteners respectively attached to the side flaps in the rear waist region so as to extend in the transverse direction and a target tape attached to the outer surface of the front waist region, on which target tape the respective tape fasteners are releasably anchored (See Japanese Laid-Open Patent Application No. 1998-309299, hereinafter referred to as Citation).

The tape fasteners have proximal portions permanently bonded to transversely outer ends of the respective side flaps and distal portions extending outward in the transverse direction from the respective proximal portions. The distal portions of the tape fasteners are provided with hooks a constituting a so-called mechanical fastener. The target tape is of a rectangular shape which is relatively long in the transverse direction and provided on its outer surface with loops constituting the mechanical fastener. A plurality of thread-like waist elastic members extending in the transverse direction are contractibly attached to the end flap in the rear waist region. A plurality of thread-like leg elastic members extending in the longitudinal direction are contractibly attached to the side flaps in the crotch region.

The diaper disposed in the foregoing Citation is put on the wearer by a parent or a care personnel in a sequence as will be described. The parent or care personnel places the hip of the wearer laid on the back on the developed diaper, then folds back the crotch region with the front waist region gripped by the wearer's fingers and places the front waist region on the wearer's belly; stretches the end flaps in the rear waist region in the transverse direction with the end flaps or the side flaps in the rear waist region gripped by the wearer's fingers; folds back the side flaps in the rear waist region with the tape fasteners gripped by the wearer's fingers so that the side flaps in the rear waist region may be laid on the wearer's belly; places the side flaps in the rear waist region upon the outer surfaces of the respective side flaps in the front waist region; and anchors the distal portions of the respective tape fasteners on the outer surface of the target tape to connect the front and rear waist regions with each other while a tightening effect of the end flaps as well as the side flaps around the wearer's waist is adjusted. To anchor the tape fasteners on the target tape, the distal portions of the respective tape fasteners may be pressed against the outer surface of the target tape to bring the hooks in engagement with the loops. Upon connection of the front and rear waist regions with each other, the diaper is formed with a waist-hole and a pair of leg-holes.

To put the diaper disclosed in the foregoing Citation on the wearer's body, the parent or care personnel develops the end flaps in the rear waist region with the end flaps or the side flaps in the rear waist region gripped by the wearer's fingers so as to stretch the waist elastic members in the transverse direction. If, however, the end flaps and/or the side flaps in the rear waist region have not a sufficient frictional force to grip the flaps firmly, it may be impossible for the parent or care personnel to stretch the waist elastic members at a desired ratio. If the waist elastic members of the diaper can not be sufficiently stretched, a contractile force of the waist elastic members can not be utilized to fasten the end flaps in the rear waist region closely around the wearer's waist. Consequently, it is likely that a gap might be left between the end flaps in the rear waist region and the wearer's skin and bodily discharges might leak out from the diaper beyond the end flaps.

SUMMARY OF THE INVENTION

In view of the problem as has been described above, it is an object of the present invention to provide a disposable diaper improved so that the waist elastic members attached to the end flaps can be sufficiently stretched when the diaper is put on the wearer's body and the contractile force of the waist elastic members can be effectively utilized to fasten the flaps closely around the wearer's waist.

The object set forth above is achieved, according to the present invention which is directed to a disposable diaper comprising: a front waist region; a rear waist region; a crotch region extending between the front and rear waist regions; a body fluid absorbing zone extending between the front and rear waist regions; a flap region extending outward beyond a peripheral edge of the absorbing zone; a first waist elastic member extending in a transverse direction contractibly attached to portions of the flap region in the rear waist region lying outside longitudinally opposite ends of the absorbing zone; a fastening means to connect the front and rear waist regions.

The diaper further comprises that antislip elements having a frictional force higher than that of the flap region and attached to the flap region in the rear waist region extending in a vicinity of transversely opposite ends of the first waist elastic member on at least one of opposite surfaces of the flap region in the rear waist region facing the wearer's skin and facing away from the wearer's skin, respectively.

The present invention may includes preferred embodiments as follow:

The antislip elements are laid on imaginary extension lines extending outward from the transversely opposite ends of the first waist elastic member.

The antislip sheets are laid on a generally entire area of the flap region in the rear waist region extending outside the side edges of the absorbing zone in the transverse direction.

A second waist elastic member extending in the transverse direction is contractibly attached to the flap region in the front waist region extending outside the longitudinally opposite ends of the absorbing zone and the antislip elements are attached to the flap region in the front waist region extending in a vicinity of transversely opposite ends of the second waist elastic member on at least one of opposite surfaces of the flap region in the front waist region facing the wearer's skin and facing away from the wearer's skin.

The antislip elements are laid on imaginary extension lines extending outward from the transversely opposite ends of the second waist elastic member.

The antislip elements are laid on a generally entire area of the flap region in the front waist region extending outside the side edges of the absorbing zone in the transverse direction.

The antislip elements have a kinetic friction coefficient in a range of 0.5 to 1.5.

The antislip elements are formed from a fibrous nonwoven fabric made of thermoplastic synthetic resin fibers having a rubber-like elasticity.

The antislip elements are formed from a fibrous nonwoven fabric made of thermoplastic synthetic resin fibers having a rubber-like elasticity and polyolefin-based thermoplastic synthetic resin fibers.

The antislip elements are colored so as to be clearly distinguished from the flap region.

The flap region comprises end flaps lying outside the longitudinally opposite ends of the absorbing zone and extending in the transverse direction and side flaps lying outside the transversely opposite side edges of the absorbing zone and extending in the longitudinal direction, and the side flaps in the rear waist region are formed from stretchy sheets which are elastically stretchable and contractible in both the longitudinal direction and the transverse direction or at least in the transverse direction.

DETAILED DESCRIPTION OF THE PREFERRED EMBODIMENTS

Details of a disposable diaper according to the present invention will be more fully understood from the description given hereunder with reference to the accompanying drawings.

Figure 1:
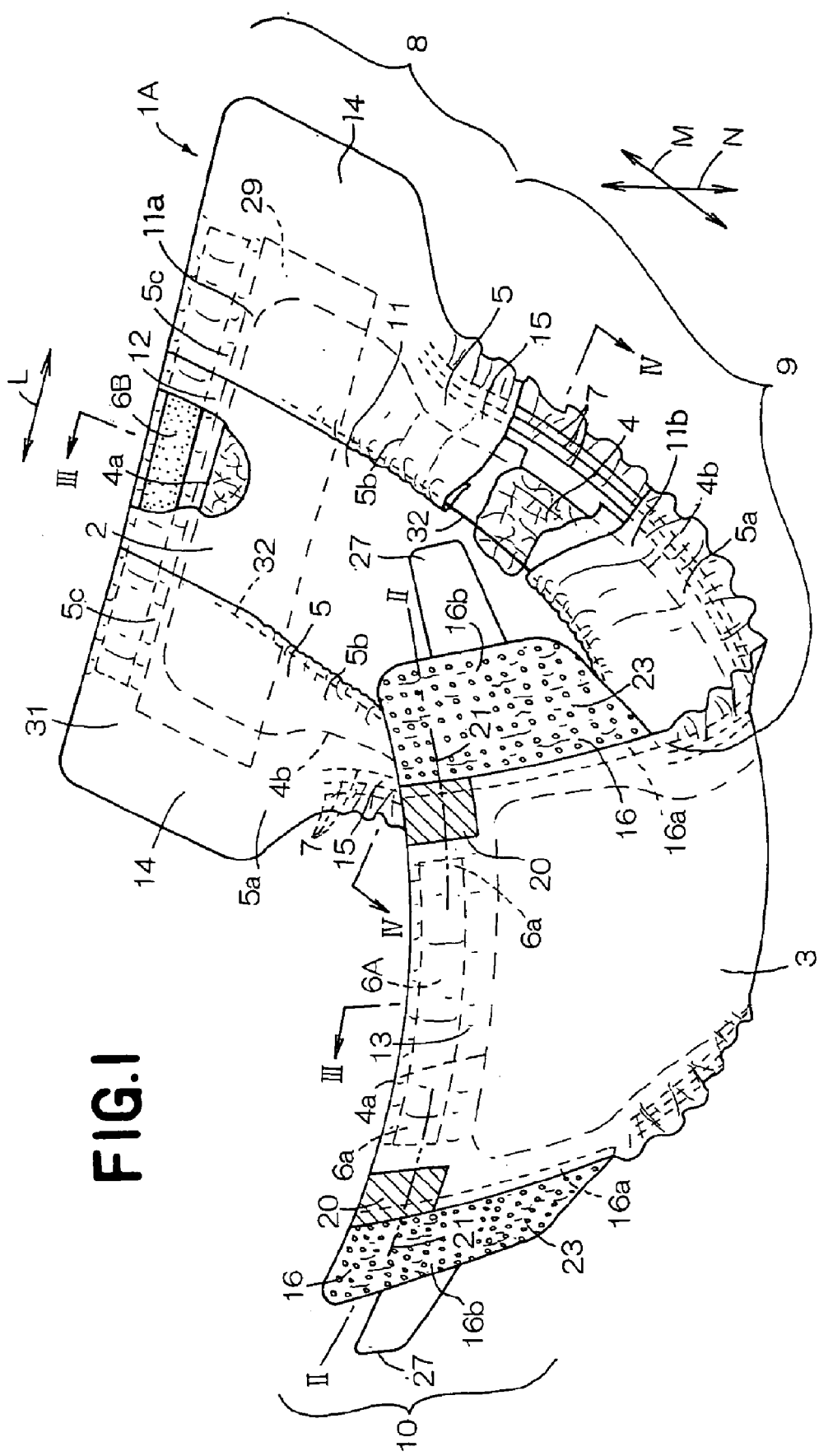
FIG. 1 is a partially cutaway perspective view depicting a diaper according to a first embodiment of the invention.
Figure 2:
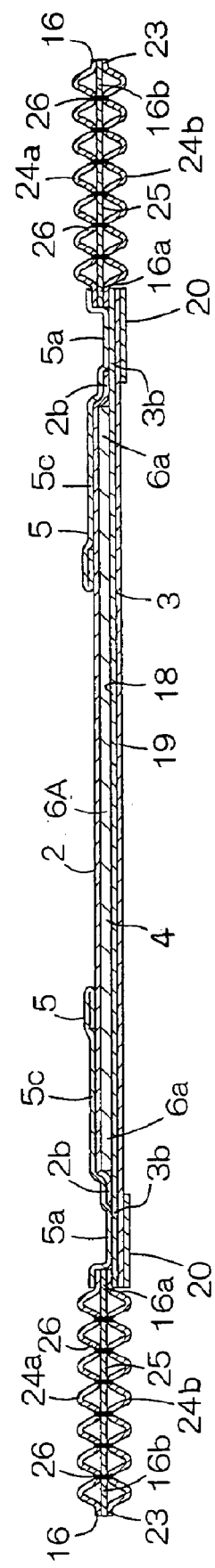
FIG. 2 is a sectional view taken along the line II-II in FIG. 1.
Figure 3:
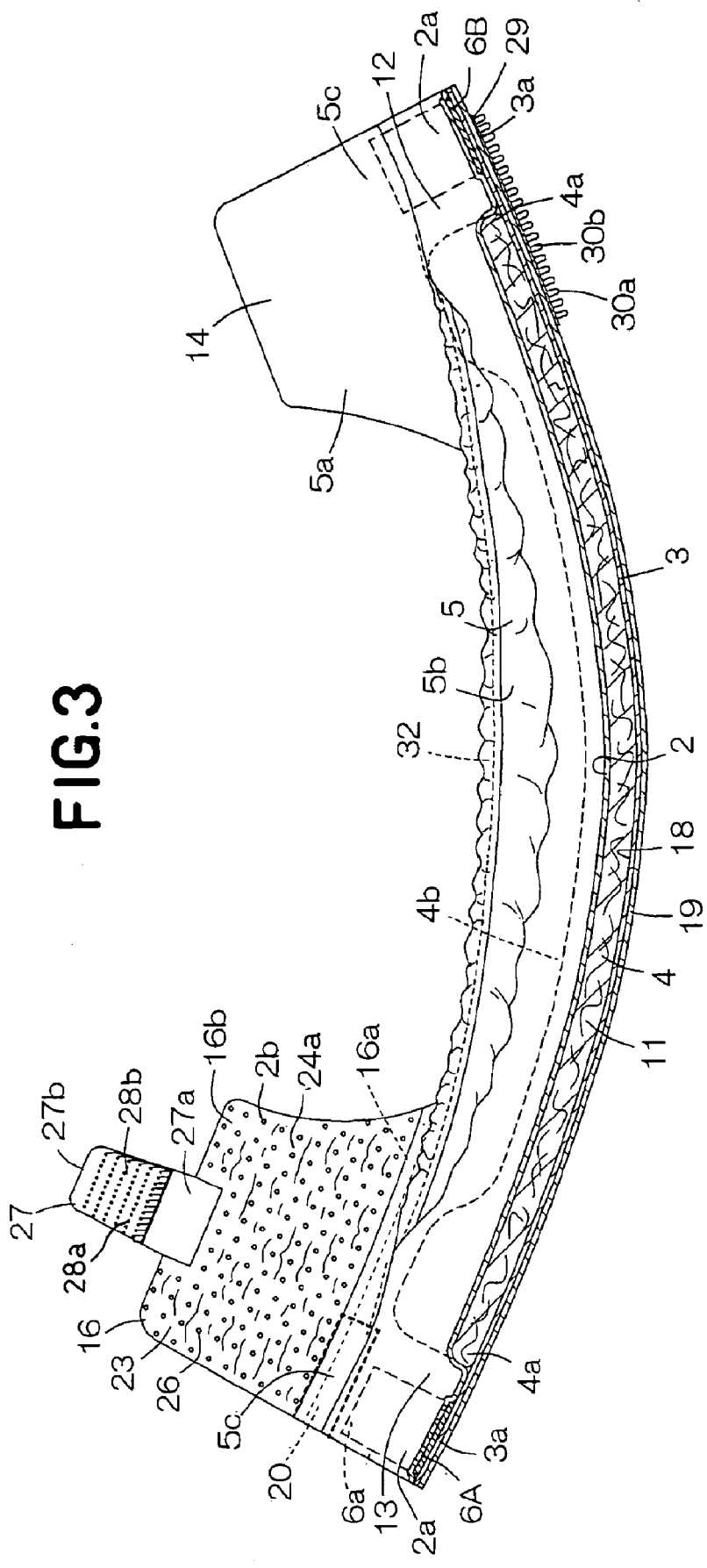
FIG. 3 is a sectional view taken along the line III-III in FIG. 1.
Figure 4:
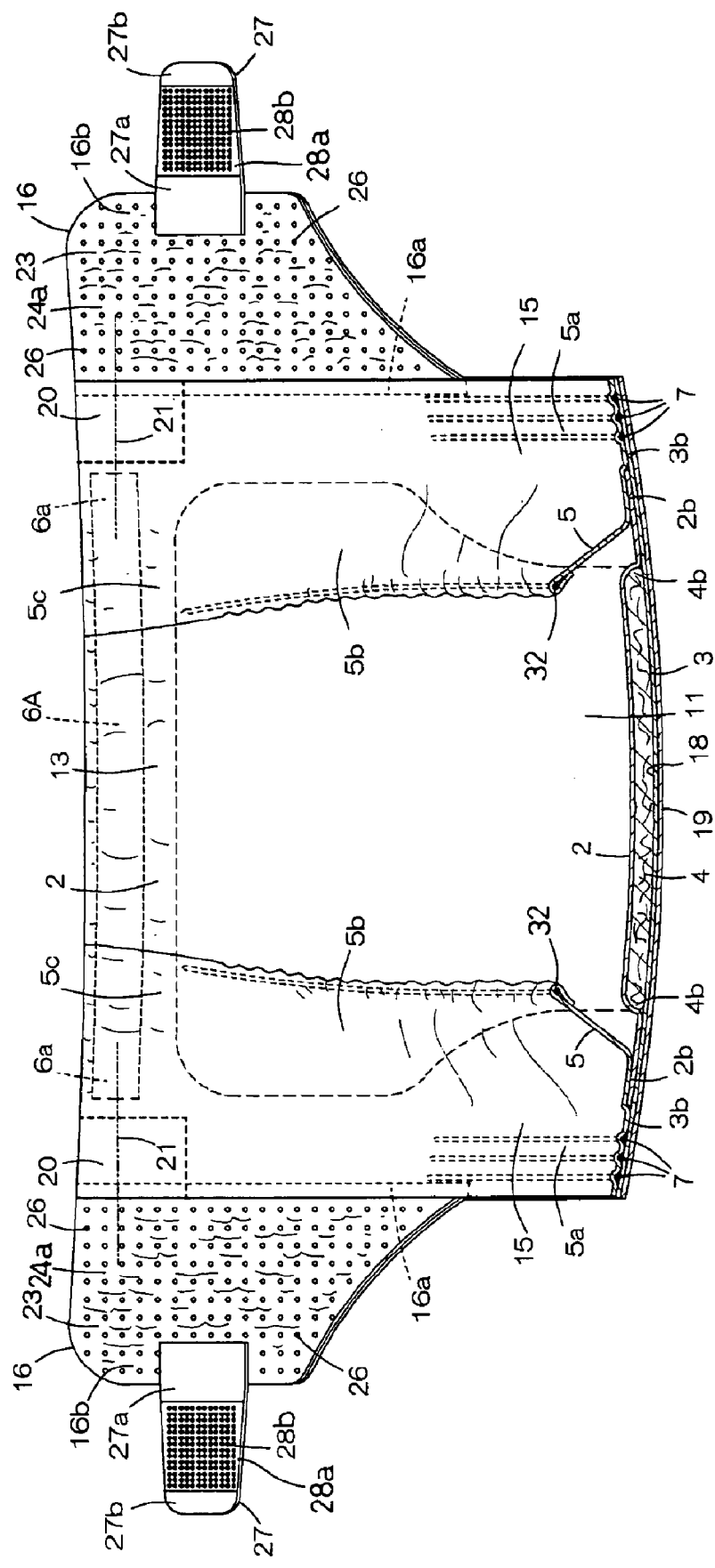
FIG. 4 is a sectional view taken along the line IV-IV in FIG. 1.

FIG. 1 is a partially cutaway perspective view depicting a diaper as a first embodiment of the invention, FIG. 2 is a sectional view taken along the line II-II in FIG. 1, FIG. 3 is a sectional view taken along the line III-III in FIG. 1 and FIG. 4 is a sectional view taken along the line IV-IV in FIG. 1. In FIG. 1, a transverse direction is indicated by an arrow L, a longitudinal direction is indicated by an arrow M and a thickness direction is indicated by an arrow N.

A diaper 1A comprises a liquid-pervious topsheet 2 facing the wearer's skin, a liquid-impervious backsheet 3 facing away from the wearer's skin, a liquid-absorbent core 4 interposed between the top- and backsheets 2, 3 and a pair of the leak-barrier flaps 5. The diaper 1A further comprises tape-like first and second waist elastic members 6A, 6B and a plurality of thread-like leg elastic members 7.

The diaper 1A defines, as viewed in the longitudinal direction, a front waist region 8, a rear waist region 10 and a crotch region 9 extending between these two waist regions 8, 10 and has a body fluid absorbing zone 11 in which the core 4 is present and a liquid-absorbing function thereof is effective, a pair of end flaps 12, 13 extending in the transverse direction outside longitudinally opposite ends 11a of the absorbing zone 11 (corresponding to longitudinally opposite ends 4a of the core 4) and a pair of side flaps 14, 15, 16 (flap regions) extending in the longitudinal direction outside transversely opposite side edges 11b of the absorbing zone 11 (corresponding to transversely opposite side edges 4b). A transverse dimension of the side flaps 14, 16 in the front and rear waist region 8, 10 is larger than a transverse dimension of the side flaps 15 in the crotch region 9, so the diaper 1A has a generally hourglass-like planar shape.

The body fluid absorbing zone 11 continuously occupies a transversely middle zone of the front waist region 8, the rear waist region 10 and the crotch region 9. In other words, the body fluid absorbing zone 11 extends, in this middle zone, over the crotch region 9 further into the front and rear waist regions 8, 10 in the longitudinal direction. The first and second waist elastic members 6A, 6B are contractibly attached to the end flaps 12, 13, respectively, so as to extend in the transverse direction. The leg elastic members 7 are contractibly attached to the side flaps 15 in the crotch region 9 so as to extend generally in the longitudinal direction.

The topsheet 2 is made of a breathable hydrophilic fibrous nonwoven fabric. The backsheet 3 is formed from inner and outer sheet 18, 19 laminated on each other and the inner sheet 18 is made of a breathable liquid-impervious plastic film and the outer sheet 19 is made of a breathable hydrophobic fibrous nonwoven fabric. Of the backsheet 3, the inner sheet 18 lies the bottom of the core 4 and the outer sheet 19 faces an undergarment of the wearer when the diaper 1A is worn. These inner and outer sheets 18, 19 have surfaces opposed to each other intermittently bonded together by means of adhesives (not shown). The core 4 is fixedly bonded to the inner surface of at least one of the top- and backsheets 2, 3.

The core 4 comprises a mixture of particulate or fibrous superabsorbent polymers and fluff pulp fibers or a mixture of particulate or fibrous superabsorbent polymers, fluff pulp fibers and thermoplastic synthetic resin fibers, in both cases, compressed to a desired thickness. Preferably, the core 4 is entirely wrapped with a liquid-pervious sheet such as a tissue paper or hydrophilic fibrous nonwoven fabric in order to prevent the core 4 from getting out of its initial shape. The polymers may be selected from the group consisting of a starch-based polymer, a cellulose-based polymer and a synthetic polymer.

The end flaps 12, 13 are defined by longitudinally opposite end portions 2a of the topsheet 2 and longitudinally opposite end portions 3a of the backsheet 3 both extending outwardly beyond the longitudinally opposite ends 4a of the core 4 in the longitudinal direction. In the end flaps 12, 13, the longitudinally opposite end portions 2a, 3a of these top- and backsheets 2, 3 are overlapped together and have the respective inner surfaces permanently bonded to each other. The waist elastic members 6A, 6B are interposed between the end portions 2a of the topsheet 2 and the end portions 3a of the backsheet 3 and permanently bonded to the respective inner surfaces of these sheets 2, 3 while these elastic members 6A, 6B are stretched at a predetermined ratio.

The end flap 13 in the rear waist region 10 is provided on their surfaces facing away from the wearer's skin with a pair of antislip elements 20 having a frictional force higher than those of both the end flap 13 and the side flaps 16. The antislip elements 20 are attached to portions of the end flap 13 extending immediately outside transversely opposite ends 6a of the first waist elastic member 6A. Specifically, these antislip elements 20 are laid on imaginary extensions 21 extending outward from the transversely opposite ends 6a of the elastic member 6A. These antislip elements 20 are permanently bonded to the outer surface of the backsheet 3 along its ends 3a by means of adhesives (not shown) applied on whole areas of the respective antislip elements 20.

Each of the antislip elements 20 has a generally rectangular planar shape which is relatively long in the longitudinal direction. Preferably, the antislip element 20 has a transverse dimension in a range of 10 to 20 mm and a longitudinal dimension in a range of 10 to 40 mm. The planar shape of the antislip element 20 is not to rectangle but may be implemented in the other shapes, e.g., a circular, oval, or triangular shape. The antislip element 20 is colored so as to be easily distinguished from a color of the end flap 13 and the side flaps 16. For example, if the end flap 13 and the side flaps 16 are of creamy white, the antislip element 20 may be colored in a chromatic color other than white. A color of the antislip element 20 is not specified and may be selected from various chromatic colors such as red, green, yellow and blue.

The antislip element 20 is formed from a sheet material such as a fibrous nonwoven fabric made of elastic fibers of thermoplastic synthetic resin having a rubber-like elasticity and inelastic fibers of thermoplastic synthetic resin. The elastic fibers are intertwined one with another and bonded together at crossover points thereof by means of a heat-sealing technique. The inelastic fibers are also intertwined one with another and bonded together at crossover points thereof by means of a heat-sealing technique. In addition, the elastic fibers and the inelastic fibers are intertwined one with another and bonded together at crossover points of these fibers by means of a heat-sealing technique.

The antislip element 20 may be obtained by a melt blowing process or spun bonding process. It is possible to form a fibrous nonwoven fabric exclusively by elastic fibers made of thermoplastic synthetic resin having a rubber-like elasticity. In this case, these elastic fibers are intertwined one with another and bonded together at the crossover points using a heat-sealing technique.

The thermoplastic synthetic resin used to form the elastic fibers may be selected from the group consisting of a styrene block copolymer, a polyurethane block copolymer, a polyester block copolymer, a polyamide block copolymer and a copolymer blend. The styrene block copolymer may be selected from the group consisting of styrene-butadiene-styrene (S-B-S) and styrene-ethylenebutadiene-styrene(S-EB-S). The copolymer blend may be selected from the group consisting of styrene-ethylenebutadiene-styrene/polypropylene(S-EB-S/PP) and polypropylene/ethylene-propylene (PP/E-P). The thermoplastic synthetic resin used to form the inelastic fibers may be polyolefin. The polyolefin may be selected from the group consisting of polyamide, polyester, polyethylene and polypropylene.

The melt blowing process is one of dry spinning type processes, comprising the steps of melt spinning thermoplastic synthetic resin, directing blast air of high temperature and high pressure toward outlets of the spinning nozzles for draft and filamentation of the fibers and collecting the fibers on a net conveyor for webbing the fibers. The fibers are accumulated on the net conveyor in the form of filaments which are heat-sealed at crossover points thereof. The fibrous nonwoven fabric (melt blown nonwoven fabric) obtained by the melt blowing process comprises extrafine fibers and has a high fiber density and a high water-resistance.

The spun bonding process also is one of the dry spinning type processes and comprising the steps of melt spinning and drawing thermoplastic synthetic resin to form a plurality of continuous fibers and collecting these continuous fibers on the net conveyor for webbing the fibers. The fibers are accumulated on the net conveyor in the form of filaments which are heat-sealed at crossover points thereof. The fibrous nonwoven fabric (spun bond nonwoven fabric) obtained by the spun bonding process is formed from continuous fibers and presents a high flexibility and high strength.

To obtain the antislip element 20 in the form of the colored fibrous nonwoven fabric, the nonwoven fabric may be immersed in a coloring material and then dried or the thermoplastic synthetic resin mixed with the coloring material may be spun.

The side flaps 16 in the rear waist region 10 is formed from a stretchy sheet 23 which is elastically stretchable and contractible in the transverse direction. The stretchy sheet 23 comprises a pair inner and outer sheets 24a, 24b and a base sheet 25 interposed those two sheets 24a, 24b. The inner and outer sheets 24a, 24b are made of a breathable hydrophobic fibrous nonwoven fabric and the base sheet 25 is made of a breathable liquid-impervious and stretchy plastic film.

The stretchy sheet 23 may be made, for example, by placing and bonding the respective inner and outer sheets 24a, 24b upon both surfaces of the stretchy base sheet 25 stretched in the transverse direction. Upon being unstressed, the base sheet 25 contracts in the transverse direction and thereby the inner and outer sheets 24a, 24b are formed with a plurality of the fine creases. The inner and outer sheets 24a, 24b and the base sheet 25 have their surfaces opposed to, placed upon and partially bonded to each other by means of a plurality of the heat-sealing spots 26 distributed generally at regular intervals. The inner and outer sheets 24a, 24b and the base sheet 25 may be bonded together using a welding technique such as a heat-sealing or sonic sealing technique. The inner and outer sheets 24a, 24b and the base sheet 25 may be intermittently bonded together not at the heat-sealing spots 26 but by means of adhesives. Of the stretchy sheet 23, the inner and outer sheets 24a, 24b are formed from inelastic fibers made of polyolefin thermoplastic synthetic resin and the base sheet 25 is formed from a thermoplastic synthetic resin having a rubber-like elasticity.

It is also possible to form each of the side flaps 16 by a single layer of inner sheet 24a of the breathable hydrophobic fibrous nonwoven fabric 24 and the base sheet 25 of the breathable liquid-impervious and stretchy plastic film. In this case, the inner sheet 24a is placed on and bonded to one surface of the base sheet 25 stretched in the transverse direction.

The side flaps 16 have their transversely outer end portions 16a interposed between transversely opposite side edges 3b of the backsheet 3 and proximal side edges 5a of the respective leak-barrier flaps 5 as will be described later in detail and transversely inner ends 16a are permanently bonded to the respective inner surfaces of backsheet 3, and the respective flaps 5 by means of adhesives (not shown). The side flaps 16 are respectively provided on their transversely opposite outer ends 16b with tape fasteners 27 extending in the transverse direction. The tape fasteners 27 have proximal portions 27a permanently bonded to the outer ends 16b of the respective side flaps 16 by means of adhesives (not shown) and distal portions 27b extending outward from the respective proximal portions 27a in the transverse direction. The tape fastener 27 is formed of a fabric of inelastic fibers made of thermoplastic synthetic resin. The distal portions 27b comprise a backing 28a and a plurality of hooks 28b protruding from the backing 28a. It should be understood that, if desired, the distal portions 27b may be coated with suitable sensitive adhesives instead of being provided with the hooks 28b.

The front waist region 8 is provided with a target zone 29 on which the distal portions 27b of the tape fasteners 27 are releasably anchored. The target zone 29 is formed from a sheet material having a rectangular planar shape which is relatively long in the transverse direction and is permanently bonded to the outer surface of the backsheet 3 by means of adhesives (not shown) intermittently or continuously. The sheet material for the target zone 29 is formed from stock materials selected from the group consisting of fibrous nonwoven fabric formed from inelastic fibers made of thermoplastic synthetic resin. The target zone 29 comprises a backing 30a and a plurality of loops 30b protruding from the backing 30a, wherein each of these loops 30b describing a circular arc. In case of the outer sheet 19 of the backsheet 3 being formed from a nonwoven fabric having substantially the same loop function as the target zone 29 comprising the backing 30a and the loops 30b, the latter element may not be used. In the embodiment of the tape fasteners 27 each having the distal portion 27b coated with pressure sensitive adhesives, the target zone 29 is formed from suitable sheet materials such as, for example, a plastic film or the like.

The side flaps 14, 15 in the front waist region 8 and the crotch region 9, respectively, are formed from transversely opposite side edges 2b, 3b of the top- and backsheets 2, 3 extending outwardly beyond the transversely opposite side edges 4b of the core 4 in the transverse direction and the proximal side edges 5a of the respective leak-barrier flaps 5. In the side flaps 14, 15, the side edges 2b of the topsheet 2 extend outwardly beyond the side edges 4b of the core 4 and the side edges 3b of the backsheet 3 as well as the side edges 5a of the leak-barrier flaps 5 extend further outwardly beyond the side edges 2b of the topsheet 2 in the transverse direction. In the side flaps 14, 15, the side edges 2b, 3b, 5a of these elements 2, 3, 5 are overlapped together and have opposed surfaces thereof permanently bonded together. The leg elastic members 7 are interposed between the side edges 3b of the backsheet 3 and the side edges 5a of the leak-barrier flaps 5 and permanently bonded to the inner surfaces of these elements 3, 5 while the leg elastic members 7 are stretched at a predetermined ratio in the transverse direction.

The leak-barrier flaps 5 are formed from a breathable hydrophobic fibrous nonwoven fabric. Each of these leak-barrier flaps 5 has a proximal side edge 5a extending on the associated side flap 14, 15, 16 in the longitudinal direction, a distal portion 5b normally biased to rise up above the topsheet 2 and extending in the longitudinal direction, and longitudinally opposite ends 5c lying on the respective end flaps 12, 13 and collapsed inwardly in the transverse direction of the diaper 1A. A stretchable elastic member 32 extending in the longitudinal direction is contractibly attached to the distal portion 5b in the vicinity of its uppermost edge. The elastic member 32 is permanently bonded to the distal portion 5b by means of adhesives (not shown) in a manner that the elastic member 32 is wrapped with a part of the distal portion 5b. The proximal ends 5c are permanently bonded to the outer surface of the topsheet 2 in the vicinity of its longitudinally opposite ends 2a. The elastic member 32 contracts as the diaper 1A curves in the longitudinal direction with the topsheet 2 inside and thereupon the distal portion 5b of the leak-barrier flaps 5 rises up above the topsheet 2. Consequently, the distal portion 5b forms a barrier against bodily discharges.

Figure 5:
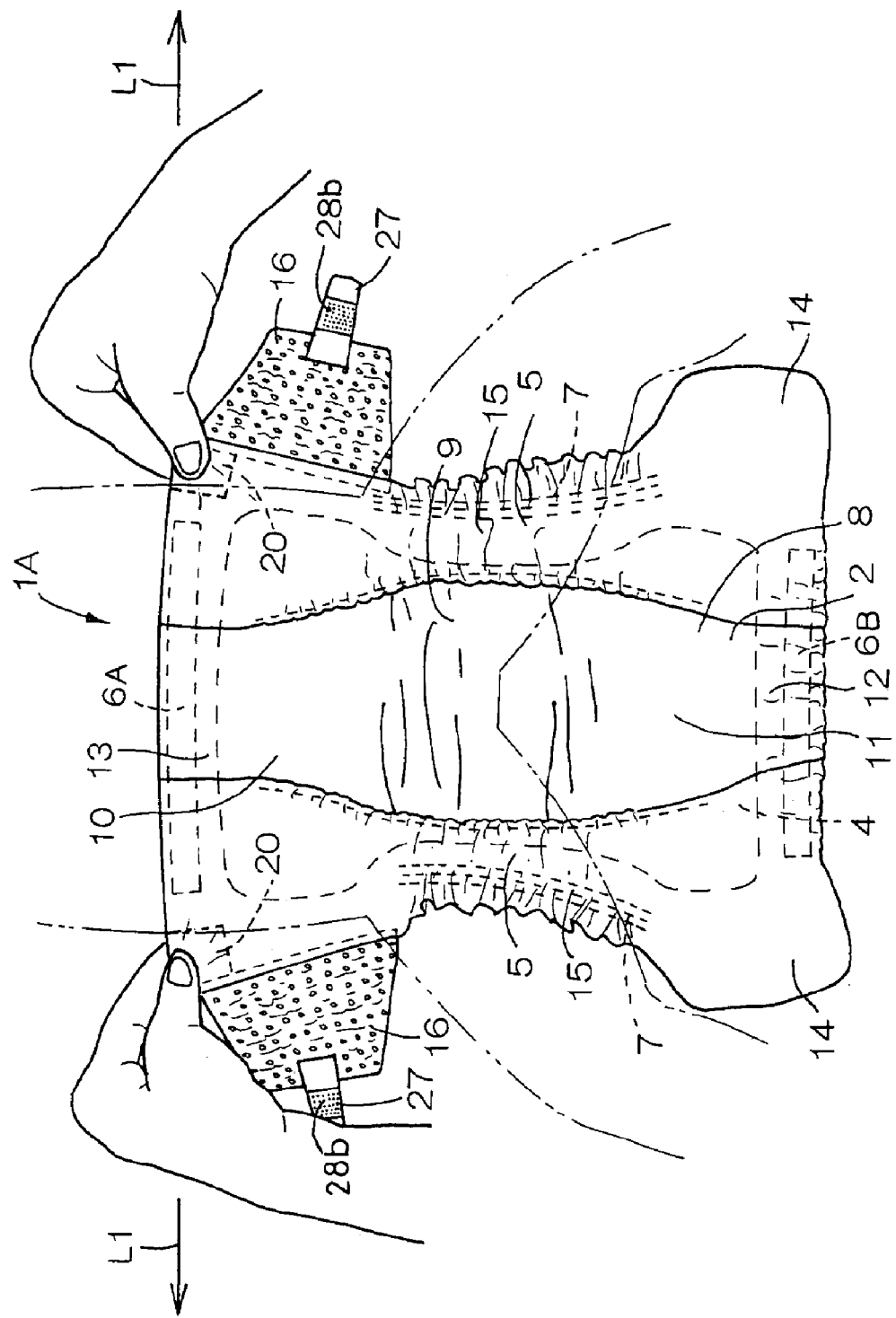
FIG. 5 is a perspective view depicting the diaper being put on a wearer's body.
Figure 6:
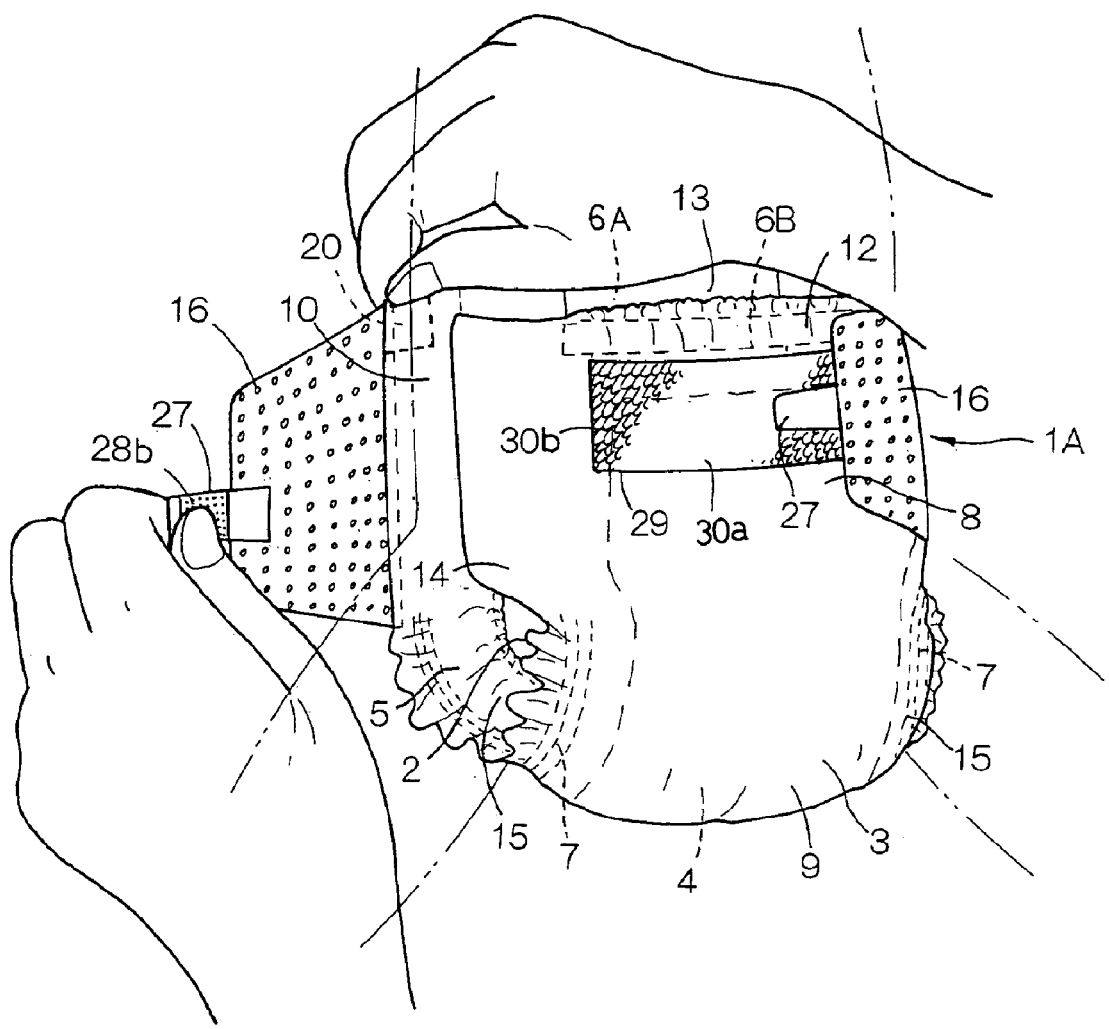
FIG. 6 is

FIGS. 5 and 6 are perspective views depicting the diaper 1A being put on the wearer's body. In FIGS. 5 and 6, the wearer is indicated by chain double-dashed line. The parent or care personnel may put the diaper 1A on the wearer's body, for example, in a sequence as follows: the hip of the wearer laid on the back is placed on the developed diaper 1A; and portions of the end flap 13 in the rear waist region 10 extending in the transverse direction immediately beyond the transversely opposite ends 6a of the first waist elastic member 6A are gripped by the wearer's fingers of both hands, respectively, so as to extend the end flap 13 in the rear waist region 10 in the transverse direction L1 and thereby to stretch the elastic member 6A in the transverse direction. In the course of putting the diaper 1A on the wearer's body, the parent or care personnel grips the antislip elements 20 attached to the flap 13 by the fingers (See FIG. 5).

After the end flap 13 has been extended, the parent or care personnel grips the front waist region 8 by the fingers and folds back the crotch region 9 of the diaper 1A so that the front waist region 8 may be placed on the wearer's belly. Then, one of the antislip elements 20 lying on the right side as viewed in FIG. 5 is gripped by the fingers of the left hand while one of the tape fasteners 27 lying on the right side as viewed in FIG. 5 is gripped by the fingers of the right hand. The end flap 13 is extended by the left hand while one of the side flaps 16 is stretched and this side flaps 16 is folded back by the right hand so that this side flap 16 may be laid on the wearer's belly. This side flap 16 is then placed upon the respective outer surfaces of the end flap 12 and the side flap 14 in the front waist region 8 and the distal portion 27b of the right side tape fastener 27 is anchored on the outer surface of the target zone 29 by means of the hooks 28b.

Now, the other of the antislip elements 20 lying on the left side as viewed in FIG. 5 is gripped by the fingers of the right hand while the other of the tape fasteners 27 lying on the left side as viewed in FIG. 5 is gripped by the fingers of the left hand (See FIG. 6). The end flap 13 is extended by the right hand while the other of the side flaps 16 is stretched and this side flaps 16 is folded back by the left hand so that this side flap 16 may be laid on the wearer's belly. This side flap 16 is then placed upon the respective outer surfaces of the end flap 12 and the side flap 14 in the front waist region 8 and the distal portion 27b of the left side tape fastener 27 is anchored on the outer surface of the target zone 29 by means of the hooks 28b while a tightness of the flaps 13, 16 around the wearer's waist is adjusted.

To anchor the tape fasteners 27 on the target zone 29, the distal portions 27b of the respective tape fasteners 27 are pressed against the outer surface of the target zone 29 and thereby the hooks 28b are brought in engagement with the loops 30b. Upon connection of the front and rear waist regions 8, 10, the diaper 1A is formed with a waist-hole and a pair of leg-holes (not shown). Body fluids discharged onto the diaper 1A put on the wearer's body are absorbed and contained by the core 4 through the topsheet 2 in the body fluid absorbing zone The presence of the antislip elements 20 adapted to be gripped by the fingers when the end flap 13 is extended in the transverse direction ensures that the parent or care personnel can put the diaper 1A on the wearer's body with the first waist elastic member 6A sufficiently stretched in the transverse direction without slippage of the fingers on the end flap 13 as has conventionally been the case. Furthermore, the contractile force of the elastic member 6A functions to tighten the end flap 13 in the rear waist region 10 closely around the wearer's waist without a possibility that a gap might be left between this end flap 13 in the rear waist region 10 and the wearer's skin and any quantity of body fluids discharged on the diaper 1A put on the wearer's body might leak out from the diaper 1A beyond the end flap 13. The antislip elements 20 lie on the imaginary extension lines 21 extending outward from the transversely opposite ends 6a of the waist elastic member 6A in the transverse direction so that the elastic member 6A can be reliably stretched in the transverse direction as the parent or care personnel extends the flap 13 in the transverse direction with the antislip element 20 gripped by the fingers. This is because a force to extend the flap 13 is directly exerted on the elastic member 6A.

The side flaps 16 in the rear waist region 10 formed from the stretchy sheet 23 are stretched in the transverse direction as the distal portions 27b of the respective tape fasteners 27 are anchored on the target zone 29, so the flaps 16 can be utilized to tighten the diaper 1A around the wearer's waist. A contractile force of the first and second waist elastic members 6A, 6B as well as of the side flaps 16 serve to tighten the end flaps 12, 13 and the side flaps 14, 16 in the front and rear waist regions 8, 10 around the wearer's waist. Consequently, there is no anxiety that these flaps 12, 13, 14, 16 might be unintentionally moved and the diaper 1A as a whole might slip down from its proper position on the wearer's body.

The antislip elements 20 are colored so as to be clearly distinguished from the colors of the flaps 13, 16 so that the parent or care personnel can reliably recognize the portions of the end flap 13 to be gripped by the fingers when the diaper 1A is put on the wearer's body. If an undergarment is put on the wearer's body over the diaper 1A, the antislip elements 20 will frictionally stick to the inner surface of the undergarment and thereby prevent the diaper 1A from slipping down.

Figure 7:
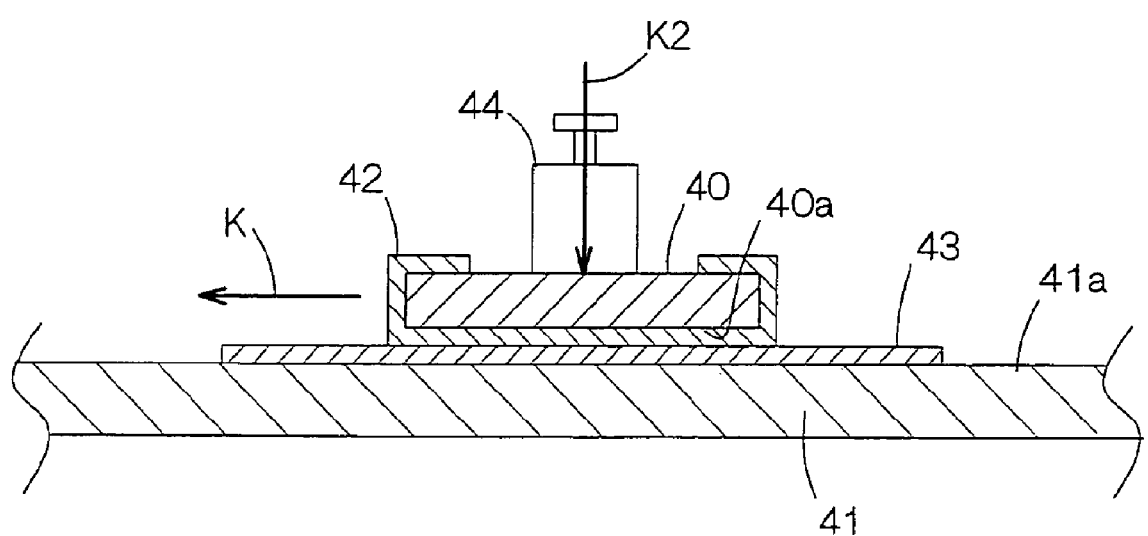
FIG. 7 is a diagram schematically illustrating how to measure a kinetic friction coefficient.

The antislip elements 20 have a kinetic friction coefficient in a range of 0.5 to 1.5 as measured in the transverse direction. If the kinetic friction coefficient of the elements 20 is less than 0.5, the fingers of the parent or care personnel gripping the end flap 13 to extend the end flap 13 in the transverse direction may slip on the flap 13 and the diaper 1A may be put on the wearer's body with the waist elastic member 6A insufficiently stretched. Kinetic friction coefficient of the antislip elements 20 was measured according to the method prescribed by Paragraph 3.1 of JIS (Japanese Industrial Standard) P8147. How to measure the kinetic friction coefficient is schematically illustrated by FIG. 7.

(1) For measurement of the kinetic friction coefficient, a movable plate 40 having a smooth lower surface 40a and a fixed plate 41 having a smooth upper surface 41a are used. The lower surface 40a of the movable plate 40 is dimensioned to have a width of 3 cm and a length of 3 cm. Sample sheet 42 of the antislip element for measurement of the kinetic friction coefficient and artificial leather, which is commercially available under the trademark "SUPPLALE" from IDEMITSU PETROCHEMICAL CO., LTD. are prepared.

(2) The sample sheet 42 is attached to the lower surface 40a of the movable plate 40 with the outer sheet 19 facing the lower surface 40a of the movable plate 40. The sample sheet 42 is bonded to the lower surface 40a of the movable plate 40 by means of a pressure sensitive adhesive double coated tape. The artificial leather 43 is attached to the upper surface 41a of the fixed plate 41. The artificial leather 43 is bonded to the upper surface 41a of the fixed plate 41 by means of a pressure sensitive adhesive double coated tape. The lower surface 40a of the movable plate 40 has a surface area of 9 cm$^2$ and a gross weight of the movable plate 40 is adjusted by counterweight 44 so that a load of 58 g/9 cm$^2$ may be exerted on the lower surface 40a.

(3) In measurement of the kinetic friction coefficient, the movable plate 40 is utilized as a poise. Referring to FIG. 7, the movable plate 40 is moved in a direction indicated by an arrow K1 at a velocity of 10 cm/min. The kinetic friction coefficient is determined on the basis of a frictional force generated as the movable plate 40 is moved by a distance of 5 cm. More specifically, the kinetic friction coefficient is calculated on the basis of an equation: $\mu = F_D/F_P$ where $\mu$ represents a kinetic friction coefficient, $F_D$ represents a frictional force generated as the movable plate 40 is moved by a distance of 5 cm and $F_D$ represents a force exerted to a contact surface of the first and second samples 42, 43 in a vertical direction indicated by an arrow K2.

The antislip elements 20 have a tensile strength in a range of 30 to 70 N/inch, a basis weight in a range of 30 to 100 g/m$^2$ and a thickness in a range of 0.2 to 0.7 mm. If the antislip elements 20 has a basis weight less than 30 g/m$^2$ and a thickness less than 0.2 mm, a tensile strength of the antislip elements 20 will become insufficient to ensure that the flap 13 can be extended without any anxiety of breakage as the flap 13 is extended in the transverse direction with the elements 20 gripped by the fingers. If the antislip elements 20 have a basis weight exceeding 100 g/m$^2$ and a thickness exceeding 0.7 mm, a stiffness of the antislip elements 20 will be unacceptably enhanced and the wearer will experience an uncomfortable feeling when the elements 20 come in contact with the wearer's skin.

The elastic fibers as well as the inelastic fibers constituting together the antislip elements 20 preferably has a fineness in a range of 0.5 to 20 μm and the inelastic fibers constituting the outer sheet 19 preferably has a fineness in a range of 10 to 20 μm. If the elastic fibers as well as the inelastic fibers has a fineness less than 0.5 μm, the fibers will be liable to breakage and a kinetic friction coefficient of the antislip elements 20 may often dip from 0.5.

The first and second waist elastic members 6A, 6B preferably have a tensile stress in a range of 0.1 to 3.0 N as measured in the transverse direction and the side flaps 16 in the rear waist region 10 preferably have a tensile stress in a range of 2.0 to 10 N as measured in the transverse direction.

If the waist elastic members 6A, 6B have a tensile stress exceeding 3.0 N and the flaps 16 have a tensile stress exceeding 10 N, the elastic members 6A, 6B and the flaps 16 will excessively tighten the wearer's waist and the wearer will experience an uncomfortable feeling due to the diaper 1A put on the wearer's body. If the waist elastic members 6A, 6B have a tensile stress less than 0.1 N and the flaps 16 have a tensile stress less than 2.0, it will be practically impossible to utilize the contractile force of the elastic members 6A, 6B and the flaps 13 in order to bring the end flaps 12, 13 and the side flaps 14, 16 in close contact with the wearer's skin.

It is possible to attach each of the antislip elements 20 to each of the end flap 13 not only on its surface facing away from the wearer's skin but also on its surface facing the wearer's skin and it is also possible to attach each of the antislip elements 20 to the end flap 13 only on its surface facing the wearer's skin. In the latter case, the elements 20 are permanently bonded to the longitudinally opposite ends 5c of the respective leak-barrier flaps 5. It is possible to attach the antislip elements 20 together with the portions of the end flap 13 extending in the vicinity of the transversely opposite ends 6a of the waist elastic member 6A to the ends 6a of the waist elastic member 6A.

Figure 8:
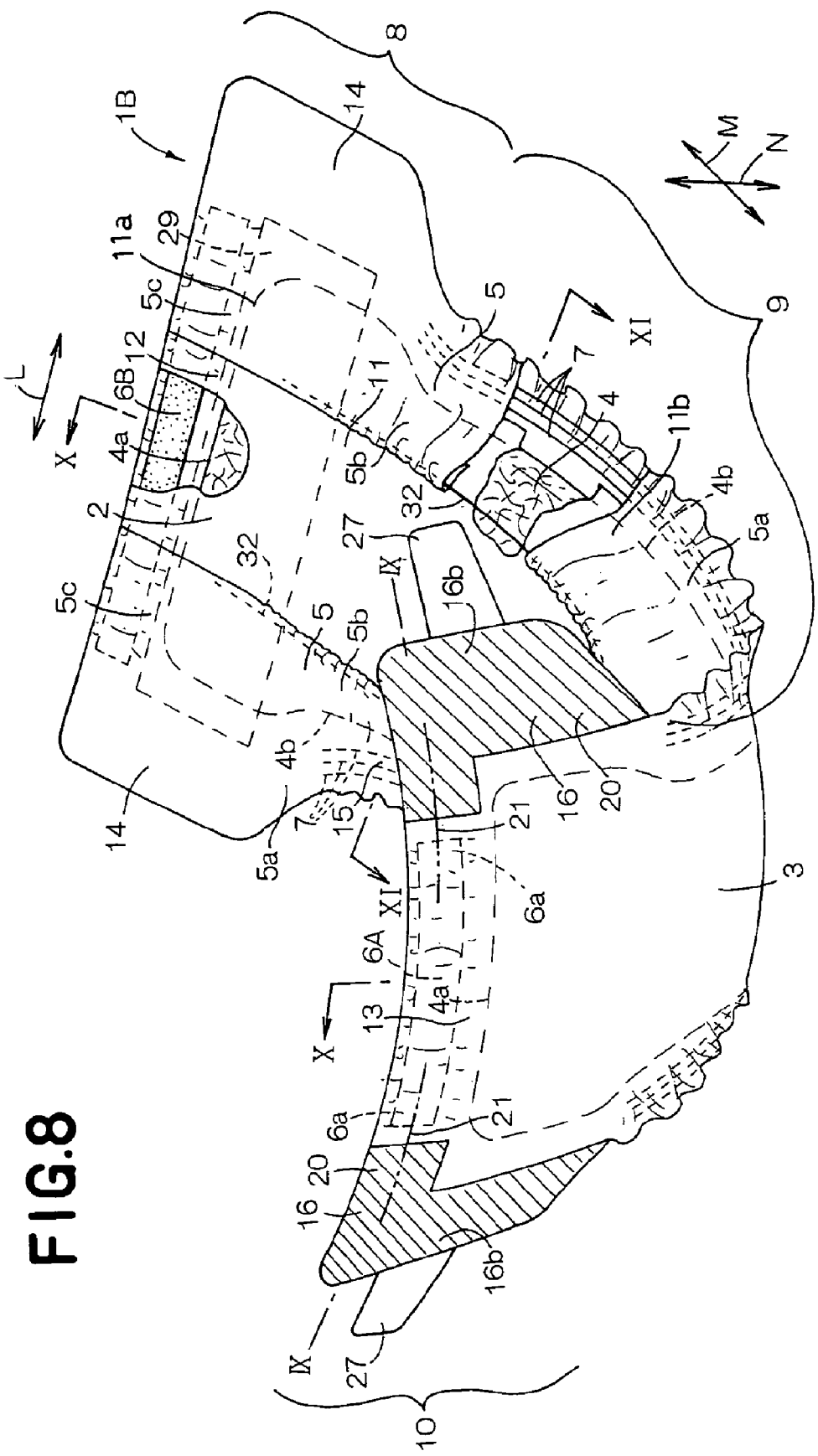
FIG. 8 is a partially cutaway perspective view depicting a diaper according to another embodiment of the invention.
Figure 9:
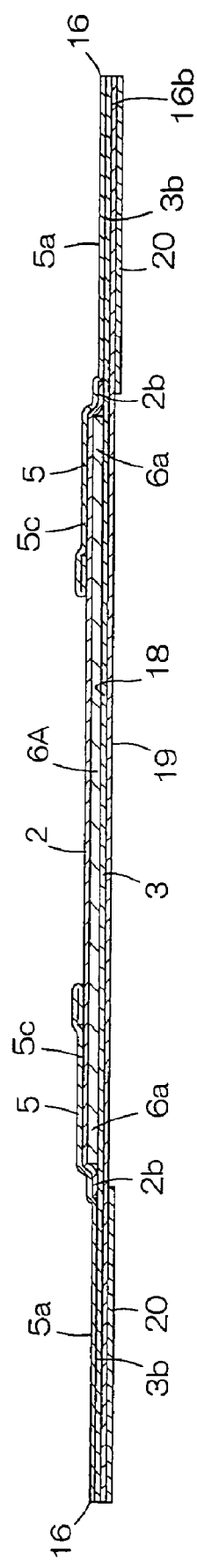
FIG. 9 is a sectional view taken along the line IX-IX in FIG. 8.
Figure 10:
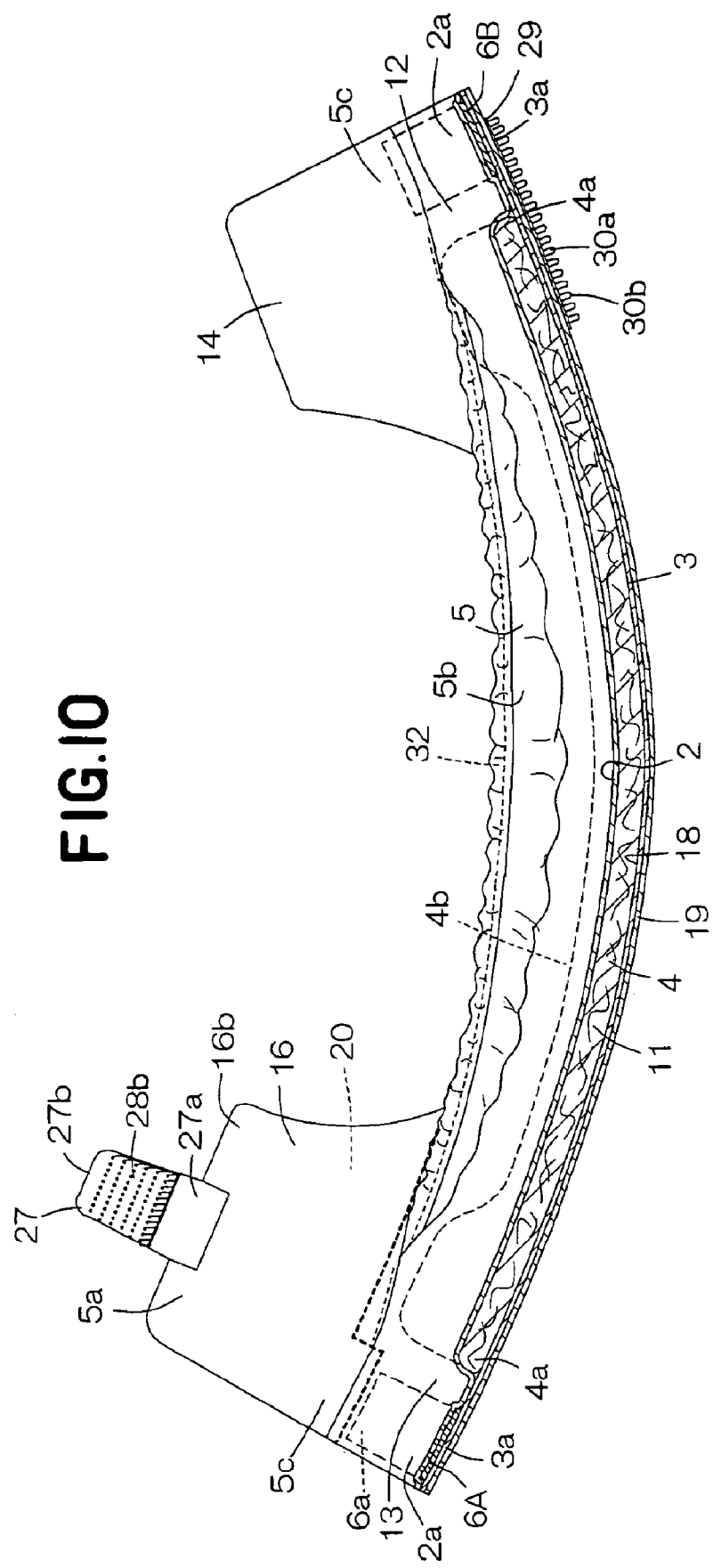
FIG. 10 is a sectional view taken along the line X-X in FIG. 8.
Figure 11:
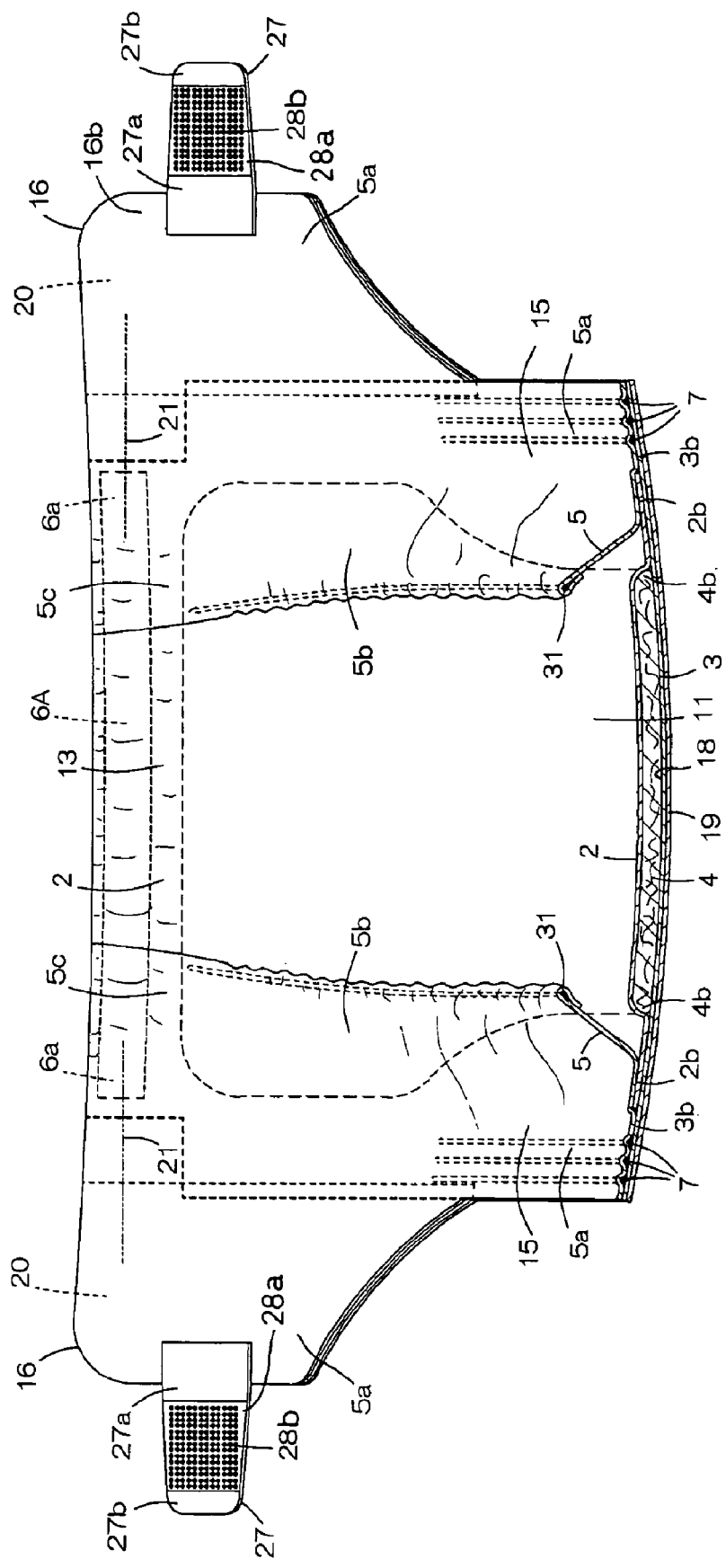
FIG. 11 is a sectional view taken along the line XI-XI in FIG. 7.

FIG. 8 is a partially cutaway perspective view depicting a diaper 1B according to another embodiment of the invention, FIG. 9 is a sectional view taken along the line IX-IX in FIG. 8, FIG. 10 is a sectional view taken along the line X-X in FIG. 8 and FIG. 11 is a sectional view taken along the line XI-XI in FIG. 8. In FIG. 8, a transverse direction is indicated by an arrow L, a longitudinal direction in indicated by an arrow M and a thickness direction is indicated by an arrow N.

In this embodiment of the present invention, components, zones and portions similar to those of the diaper 1A previously described are denoted by the same reference numeral and the description of the same components, etc. are here omitted to avoid the repetition thereof, that is, the different components, etc. alone are explanated.

The side flaps 14, 15, 16 extend in the longitudinal direction outside transversely opposite side edges 11b of the absorbent zone 11 and are formed from transversely opposite side edges 2b, 3b of the top- and backsheets 2, 3 and fixed side edges 5a of the respective leak-barrier flaps 5 all extending outward beyond transversely opposite side edges 4b of the core 4. In the side flaps 14, 15, 16, the side edges 2b extend outwardly slightly beyond the side edges 4b of the core 4 and the side edges 3b of the backsheet 3 as well as the side edges 5a of the leak-barrier flaps 5 extend further outward beyond the side edges 2b of the topsheet 2 in the transverse direction. In the side flaps 14, 15, 16, the side edges 2b, 3b, 5a of these sheets 2, 3, 5 are overlapped together and have opposed surfaces thereof permanently bonded together. The leg elastic members 7 are interposed between the side edges 3b of the backsheet 3 and the side edges 5a of the leak-barrier flaps 5 and permanently bonded to the inner surfaces of these elements 3, 5.

An end flap 13 and the side flaps 16 in the rear waist region 10 are respectively provided on their surfaces facing away from the wearer's skin with a pair of antislip elements 20 having a frictional force higher than those of both the end flap 13 and the side flaps 16. The antislip elements 20 are attached to the end flap 13 on zones extending immediately outside transversely opposite ends 6a of the first waist elastic member 6A and to the side flaps 16 over generally entire areas thereof. Specifically, these elements 20 attached to the end flap 13 are laid on imaginary extensions 21 extending outward from the transversely opposite ends 6a of the elastic member 6A. These elements 20 are permanently bonded to the outer surface of the backsheet 3 along its ends 3a forming the end flap 13 by means of adhesives (not shown) on whole areas of the respective elements 20. The elements 20 are colored so as to be easily distinguished from a color of the end flap 13 and the side flaps 14, 15, 16 as in the case of the diaper 1A shown in FIG. 1.

The antislip elements 20 attached to the side flaps 16 on the respective surfaces facing away from the wearer's skin are effective to prevent the fingers gripping the side flaps 16 from slipping thereon as the side flaps 16 are extended and to facilitate the diaper 1B to be put on the wearer's body. In addition, the antislip elements 20 facilitate a tightness of the end flap 13 as well as of the side flaps 16 around the wearer's waist to be adjusted. If an underwear is put on the wearer's body over the diaper 1B, the antislip elements 20 will frictionally stick to the inner surface of the underwear and thereby prevent the diaper 1B from slipping down.

The antislip elements 20 may be attached to the end flap 13 and the side flaps 16 on both the surfaces facing away from the wearer's skin and the surfaces facing the wearer's skin of these flaps 13, 16 or exclusively on the respective surfaces of these flaps 13, 16 facing the wearer's skin.

Figure 12:
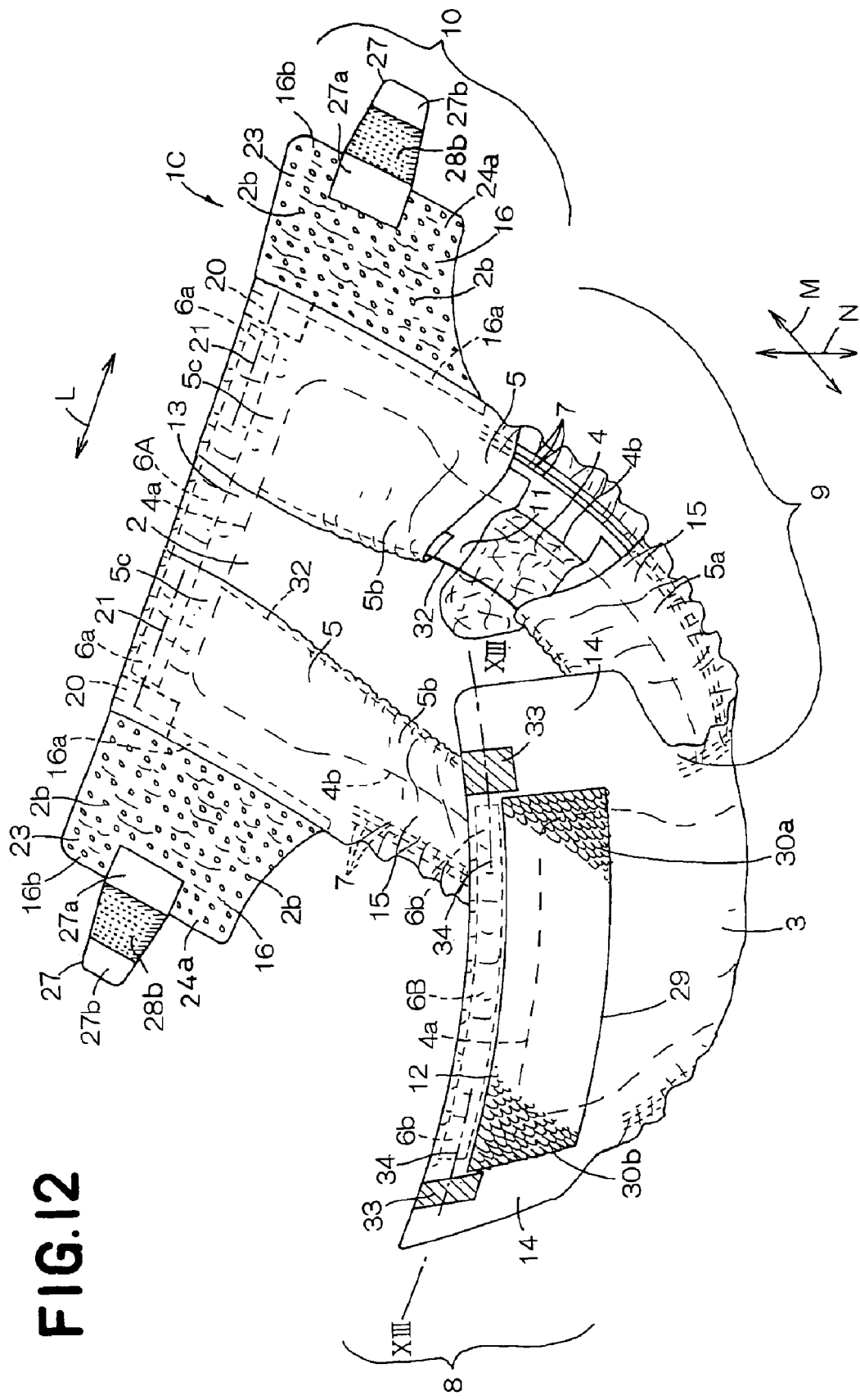
FIG. 12 is a partially cutaway perspective view depicting a diaper according to a second embodiment of the invention.
Figure 13:
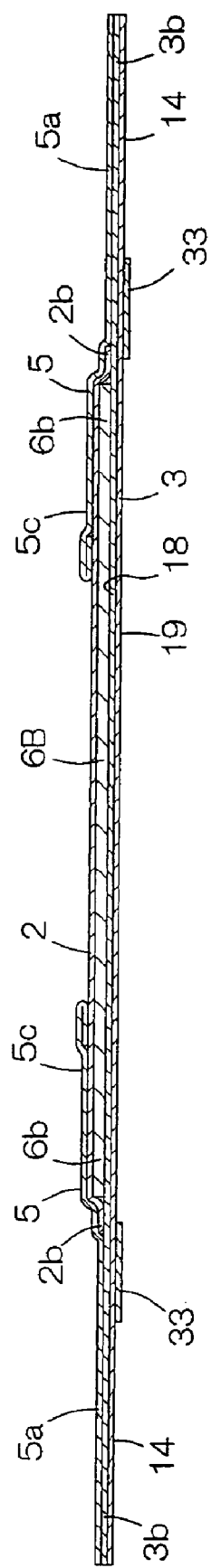
FIG. 13 is a sectional view taken along the line XIII-XIII in FIG. 12.
Figure 14:
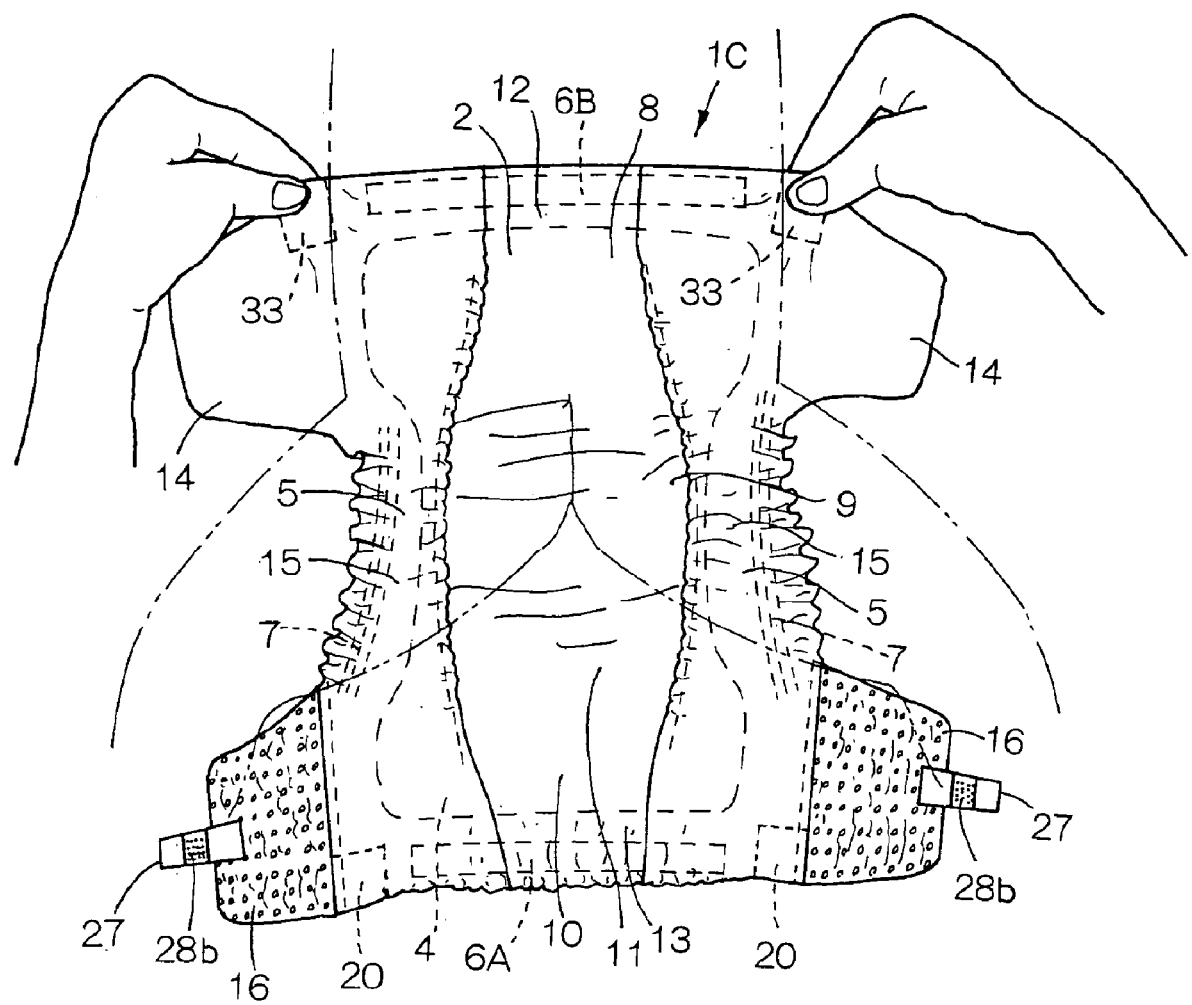
FIG. 14 is a perspective view depicting the diaper being put on a wearer's body.
Figure 15:
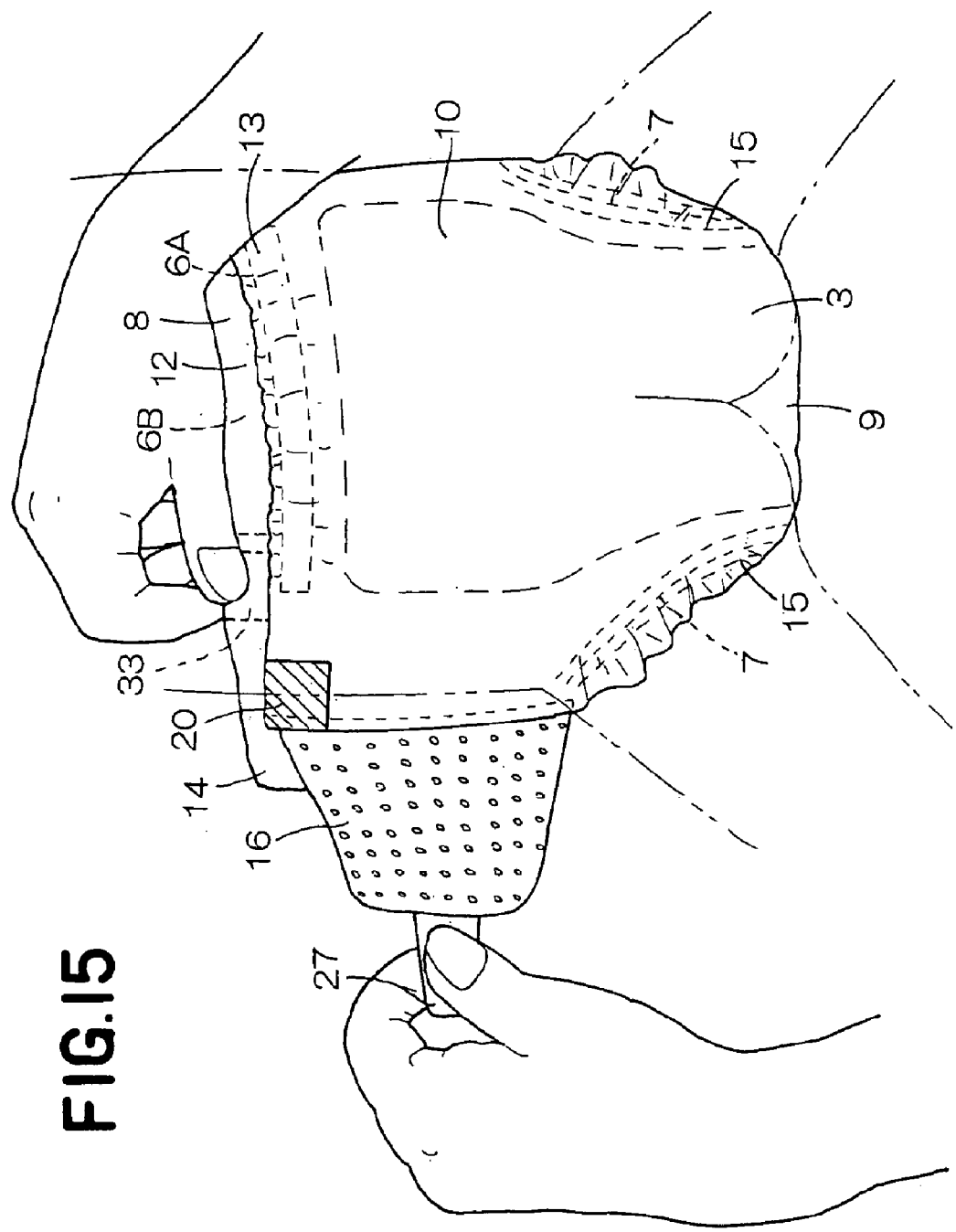
FIG. 15 is a perspective view depicting the diaper being put on a wearer's body.

FIG. 12 is a partially cutaway perspective view depicting a diaper 1C according to further another embodiment of the invention, FIG. 13 is a sectional view taken along the line XIII-XIII in FIG. 12, and FIGS. 14 and 15 are perspective views depicting the diaper 1C being put on the wearer's body. In FIG. 12, a transverse direction is indicated by an arrow L, a longitudinal direction is indicated by an arrow M and a thickness direction is indicated by an arrow N. In FIGS. 14 and 15, the wearer is indicated by a chain double-dashed line.

This diaper 1C is distinguished from the diaper 1A depicted in FIG. 1 in that additional antislip elements 33 are attached to the end flap 12 of the diaper 1A. The remaining features of the diaper 1C are similar to those of the diaper 1A depicted in FIG. 1 and the components, zones and portions similar to those of the diaper 1A are denoted by the same numeral, respectively and the detailed description thereof is omitted here.

The end flap 12 in the front waist region 8 is respectively provided on its surface facing away from the wearer's skin with a pair of antislip elements 33 having a frictional force higher than that of the end flap 12. The antislip elements 33 are attached to portions of the end flap 12 extending immediately outside transversely opposite ends 6b of the second waist elastic member 6B. Specifically, these elements 33 are laid on imaginary extensions 34 extending outward from the transversely opposite ends 6b of the elastic member 6B and are permanently bonded to the outer surface of the backsheet 3 along its ends 3a by means of adhesives (not shown) applied on whole areas of the respective elements 33.

Similarly to those of the diaper 1A depicted in FIG. 1, the antislip elements 33 are formed by a fibrous nonwoven fabric made of elastic fibers of thermoplastic synthetic resin having a rubber-like elasticity or by a fibrous nonwoven fabric or made of elastic fibers of thermoplastic synthetic resin having a rubber-like elasticity and inelastic fibers of thermoplastic synthetic resin.

Each of the antislip elements 33 has a generally rectangular planar shape which is relatively long in the longitudinal direction. The antislip elements 33 are colored so as to be easily distinguished from a color of the end flap 12 and the side flaps 14. The antislip elements 20, 33 may be attached to the end flaps 12, 13 on the respective surfaces thereof not only facing away from the wearer's skin but also facing the wearer's skin or may be attached to these flaps 12, 13 exclusively on the respective surfaces thereof facing the wearer's skin.

The parent or care personnel may put the diaper 1C on the wearer's body, for example, in a sequence as follows: the belly of the wearer laid facedown is placed on the developed diaper 1C; and portions of the end flap 12 in the front waist region 8 extending in the transverse direction immediately beyond the transversely opposite ends 6b of the first waist elastic member 6B are gripped by the fingers of both hands, respectively, so as to extend the end flap 12 in the front waist region 8 in the transverse direction L2 and thereby to stretch the elastic member 6B in the transverse direction. In the course of putting the diaper 1C on the wearer's body, the parent or care personnel grips the antislip elements 33 attached to the flap 12 by the fingers (See FIG. 14).

After the end flap 12 has been extended, the parent or care personnel grips the rear waist region 10 by the fingers and folds back the crotch region 9 of the diaper 1C so that the rear waist region 10 may be placed on the wearer's hip. Then, one of the antislip elements 33 lying on the right side as viewed in FIG. 5 is gripped by the fingers of the left hand while the other of the tape fasteners 27 lying on the right side as viewed in FIG. 5 is gripped by the fingers of the right hand. The end flap 12 is extended by the left hand while one of the side flaps 16 is stretched and this side flaps 16 is folded back by the right hand so that this side flap 16 may be laid on the wearer's belly. This side flap 16 is then placed upon the respective outer surfaces of the end flap 12 in the front waist region 8 and the side flap 14 in the front waist region 8 and the distal portion 27*b* of the right side tape fastener 27 is anchored on the outer surface of the target zone 29 by means of the hooks 28*b*.

Now, the other of the antislip sheets 33 lying on the left side as viewed in FIG. 5 is gripped by the fingers of the right hand while the other of the tape fasteners 27 lying on the left side as viewed in FIG. 5 is gripped by the fingers of the left hand (See FIG. 15). The end flap 12 is extended by the right hand while the other of the side flaps 16 is stretched and folded back by the left hand so that this side flap 16 may be laid on the wearer's belly. This side flap 16 is then placed upon the respective outer surfaces of the end flap 12 and the side flap 14 in the front waist region 8 and the distal portion 27*b* of the left side tape fastener 27 is anchored on the outer surface of the target zone 29 by means of the hooks 28*b* while a tightness of the flaps 13, 16 around the wearer's waist is adjusted.

Figure 16:
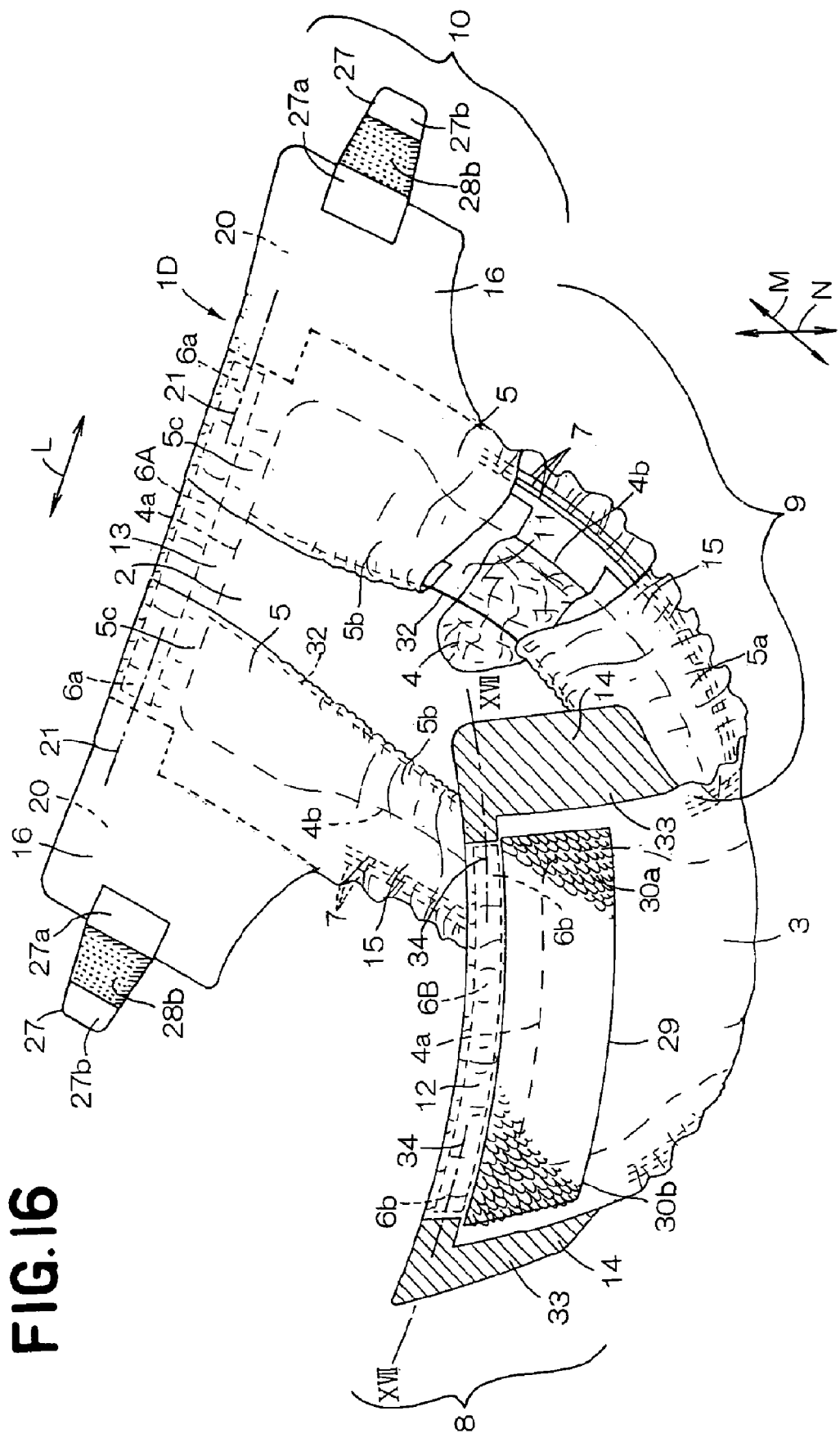
FIG. 16 is a perspective view depicting a diaper according to a third embodiment of the invention.
Figure 17:
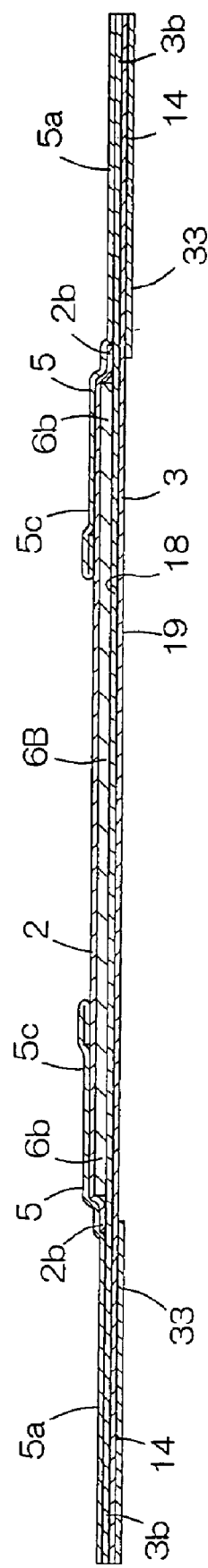
FIG. 17 is a sectional view taken along the line XVII-XVII in FIG. 16.

FIG. 16 is a partially cutaway perspective view showing a diaper 1D according to still another embodiment of the invention and FIG. 17 is a sectional view taken along the line XVII-XVII in FIG. 16. In FIG. 16, a transverse direction is indicated by an arrow L, a longitudinal direction is indicated by an arrow M and a thickness direction is indicated by an arrow N.

This diaper 1D is distinguished from the diaper 1B depicted in FIG. 8 in that additional antislip elements 33 are attached to the end flap 12 of the diaper 1B. The remaining features of the diaper 1D are similar to those of the diaper 1B depicted in FIG. 8 and the components, zones and portions similar to those of the diaper 1B are denoted by the similar reference numeral, respectively and the detailed description thereof is omitted here.

The end flap 12 and the side flaps 14 in the front waist region 8 are respectively provided on their surfaces facing away from the wearer's skin with antislip elements 33 having a frictional force higher than those of these flaps 12, 14. The antislip elements 33 are attached to portions of the end flap 12 extending immediately outside transversely opposite ends 6*b* of the second waist elastic member 6B and the side flaps 14 over generally entire areas of these side flaps 14. Specifically, these elements 33 attached to the end flap 12 are laid on imaginary extensions 34 extending outward from the transversely opposite ends 6*b* of the elastic member 6B. These elements 33 are permanently bonded to the outer surface of the backsheet 3 along its ends 3*a* and the outer surface of the side edges 3*b* of the backsheet 3 by means of adhesives (not shown) applied on whole areas of the respective elements 33.

The antislip elements 20, 33 may be attached to the end flaps 12, 13 and the side flaps 14, 16 on both the surfaces facing away from the wearer's skin and the surfaces facing the wearer's skin of these flaps or exclusively on the respective surfaces of these flaps 12, 13, 14, 16 facing the wearer's skin.

The antislip elements 33 have a kinetic friction coefficient in a range of 0.5 to 1.5. If the kinetic friction coefficient of the elements 20 is less than 0.5, the fingers of the parent or care personnel gripping the end flap 12 in order to extend the end flap 12 in the transverse direction may slip on the flap 12 and the diaper 1C, 1D may be put on the wearer's body with the waist elastic member 6B insufficiently stretched.

Kinetic friction coefficient of the antislip elements 33 is measured by the same method as for the diaper 1A shown by FIG. 1. Finenesses of the elastic fibers as well as of the inelastic fibers constituting the elements 33 is same as that in the diaper 1A depicted in FIG. 1. Stretching stresses of the first and second waist elastic members 6A, 6B in the diapers 1C, 1D as measured in the transverse direction are the same as those in the diaper 1A depicted in FIG. 1.

Stock materials for the topsheet 2 may be selected from the group consisting of a hydrophobic fibrous nonwoven fabric having a plurality of apertures and a plastic film having a plurality of fine perforations. Stock materials for the backsheet 3 may be selected from the group consisting of a breathable hydrophobic fibrous nonwoven fabric, a breathable liquid-impervious plastic film and a composite nonwoven fabric comprising two or more breathable hydrophobic fibrous nonwoven fabric layers laminated one upon another. Stock materials for the leak-barrier flaps 5 may be selected from the group consisting of a composite nonwoven fabric comprising two or more breathable hydrophobic fibrous nonwoven fabric layers laminated one upon another and a composite sheet comprising a breathable hydrophobic fibrous nonwoven fabric and a breathable liquid-impervious plastic film laminated upon each other.

As stock materials for the backsheet 3 and the leak-barrier flaps 5, it is also possible to use a composite nonwoven fabric (SM nonwoven fabric or SMS nonwoven fabric) consisting of a melt blown fibrous nonwoven fabric having a high water-resistance and a spun bond fibrous nonwoven fabric having a high strength as well as a high flexibility laminated on at least one side of the melt blown fibrous nonwoven fabric.

The fibrous nonwoven fabric used to form the top- and backsheets 2, 3, the leak-barrier flaps 5, the side flaps 16 in the rear waist region 10, the tape fasteners 27 and the target zone 29 made of the sheet material may be selected from those obtained by spun lace-, needle punch-, melt blown-, thermal bond-, spun bond- and chemical bond-processes.

The hydrophilic fibrous nonwoven fabric may be made of any one of synthetic fibers, semi-synthetic fibers and regenerated fibers each modified to become hydrophilic or conjugate fibers thereof. The hydrophobic fibrous nonwoven fabric may be formed by synthetic fibers and may contain therein semi-synthetic fibers or regenerated fibers both treated to become water repellent. While not specified, the synthetic fibers may be selected from the group consisting of polyester-, polyacrylonitrile-, polyvinyl chloride-, polyethylene-, polypropylene- and polystyrene-based fibers. The suitably useful synthetic fibers further include core-sheath type conjugate fibers, side-by-side type conjugate fibers, macaroni fibers, microporous fibers and bonded-type conjugate fibers.

It is preferred to use hot melt adhesives as the adhesives. In addition to the hot melt adhesive, it is also possible to use any one of acrylic adhesives and elastomeric adhesives. The adhesives may be applied on the top- and backsheets 2, 3 and the leak-barrier flaps 5 in a suitable pattern selected from the group consisting of a spiral pattern, a zigzag pattern, a dotted pattern and a striped pattern. Application of the adhesives on these elements 2, 3, 5 in such pattern generates adhesive-coated regions and adhesive-free regions, resulting in that these elements 2, 3, 5 are permanently bonded one to another in intermittent fashion, the elements 2, 3, 5 are bonded to one to another in an intermittent fashion and the core 4 is permanently bonded to the sheets 2, 3.

In the case of the disposable diaper according to the present invention, the portions of the flap region in the rear waist region extending in the vicinity of the transversely opposite ends of the first waist elastic member are provided with the antislip elements. These antislip elements ensures that the parent or care personnel can put the diaper on the wearer's body with the first waist elastic member attached to the flap region in the rear waist region sufficiently stretched in the transverse direction without an anxiety that the fingers gripping the flap region might slip on the flap region when the parent or care personnel extends the flap region in the rear waist region in the transverse direction. The contractile force of the first waist elastic member tightens the flap region in the rear waist region extending in the transverse direction around the wearer's waist without leaving any gap between the flap region and the wearer's skin. As a result, it is unlikely that any quantity of body fluids discharged on the diaper put on the wearer's body might leak out beyond the flap region.

In the case of the diaper having the antislip elements lying on the imaginary extension lines extending outward from the transversely opposite ends of the first waist elastic member, the force with which the flap region is extended in the transverse direction is exerted directly upon the first waist elastic member and ensures that the elastic member can be reliably stretched.

In the case of the diaper having the antislip elements attached to the flap region in the rear waist region lying outside the transversely opposed side edges of the absorbing zone over the generally entire area of this flap region, the fingers surely come in contact with the antislip elements so far as the flap region is gripped by the fingers and slippage of the fingers on the flap region can be reliably prevented.

In the case of the diaper having the antislip elements to the flap region in the front waist region which extends in the vicinity of the transversely opposite ends of the second waist elastic member, these antislip elements ensure that the parent or care personnel can put the diaper on the wearer's body with the second waist elastic member sufficiently stretched in the transverse direction without slippage of the fingers on the end flap when the flap region is extended in the transverse direction. The contractile force of the second elastic member functions to tighten the flap region in the front waist region closely around the wearer's waist without a possibility that a gap might be left between this flap region and the wearer's skin and any quantity of body fluids discharged on the diaper put on the wearer's body might leak out from the diaper beyond this flap region.

In the case of the diaper having the antislip elements lying on the imaginary extension lines extending outward from the transversely opposite ends of the second waist elastic member in the transverse direction, so the elastic member can be reliably stretched in the transverse direction as the parent or care personnel extends the flap in the transverse direction with the antislip elements gripped by the fingers since a force to extend the flap is directly exerted on the second waist elastic member.

In the case of the diaper having the antislip elements attached to the flap region in the front waist region lying outside the transversely opposite side edges of the absorbing zone over the substantially entire area of this flap region, slippage of the fingers gripping the flap region can be reliably prevented.

In the case of the diaper having the antislip elements colored so as to be clearly distinguished from the flap region, the positions at which the flap region should be gripped by the fingers can be reliably recognized by the parent or care personnel which puts the diaper on the wearer's body.

In the case of the diaper having the flap region comprising the end flaps and the side flaps wherein the side flaps in the rear waist region is formed from the stretchy sheet, the flap region can be utilized to tighten the diaper around the wearer's waist because the side flaps in the rear waist region is stretched in the transverse direction as the front and rear waist regions are connected with each other by the fastening means. In addition, the contractile force of the waist elastic members and the side flaps functions to bring the end flaps and the side flaps in close contact with the wearer's skin and thereby to eliminate a possibility that these flaps might be moved relatively one to another and the diaper might slip down from its proper position on the wearer's body.

What is claimed is:

1. A disposable diaper, comprising:
   a diaper structure comprising
      a front waist region, a rear waist region, a crotch region extending in a longitudinal direction of said diaper structure between said front and rear waist regions,
      an absorbent core in at least said crotch region,
      each of said front and rear waist regions including transversely opposed side flap regions on transversely opposite sides of said absorbent core, and
      a rear waist elastic member for elasticizing the rear waist region in a transverse direction of said diaper structure, said rear waist elastic member extending in the rear waist region, in the transverse direction of said diaper structure, and being rearwardly spaced from a rear end of said absorbent core;
   a pair of tape fasteners adapted to releasably attach said front waist region to said rear waist region, said tape fasteners being respectively attached to the transversely opposite side flap regions of the rear waist region; and
   antislip elements being immovably fixed to said diaper structure in the rear waist region and at locations adjacent to opposite ends of said rear waist elastic member, said antislip elements having a frictional force higher than that of the side flap regions of the rear waist region, thereby facilitating manual gripping of said diaper structure in the rear waist region and stretching of said rear waist elastic member in the transverse direction while the diaper is being put on a wearer;
   wherein
   said diaper structure comprises an inner surface which is adapted to face, in use, toward the wearer, said inner surface of said diaper structure being free of said antislip elements;
   said diaper structure further comprises an outer surface which is adapted to face, in use, away from the wearer, said antislip elements being attached to the outer surface of said diaper structure;
   each of said tape fasteners comprises a distal end carrying fastening members engageable with the outer surface of said diaper structure in the front waist region, and a proximal end free of said fastening members and inwardly spaced from said distal end in the transverse direction; and
   the proximal end of each said tape fastener is attached to the inner surface of said diaper structure in an area corresponding to the respective one of said antislip elements so as to overlay said respective antislip element which, in turn, is completely spaced inwardly from the fastening members carried at the distal end of the respective tape fastener.

2. The diaper according to claim 1, wherein said antislip elements extend up to longitudinally opposite side edges of said diaper structure.

3. The diaper according to claim 1, wherein
   said diaper structure has a shape of a hourglass, said shape comprising a main portion elongated in the longitudinal direction and four ear portions positioned on transversely opposite sides of said main portion in the front and rear waist region; and said antislip elements occupy entirely the outer surface of the ear portions in the rear waist region.

4. The diaper according to claim 1, wherein said antislip elements are formed from a fibrous nonwoven fabric made of thermoplastic synthetic resin fibers having elasticity.

5. The diaper according to claim 4, wherein said antislip elements have a kinetic friction coefficient in a range of 0.5 to 1.5.

6. The diaper according to claim 5, wherein said antislip elements are generally flat.

7. The diaper according to claim 1, wherein said antislip elements are formed from a fibrous nonwoven fabric made of thermoplastic synthetic resin fibers having elasticity and polyolefin-based thermoplastic synthetic resin fibers.

8. The diaper according to claim 6, wherein said antislip elements are colored so as to be visually distinguished from the respective side flap regions of said rear waist region.

9. The diaper according to claim 5, wherein the side flap regions of said rear waist region are elastically stretchable and contractible at least in the transverse direction.

10. The diaper according to claim 1, wherein said antislip elements are fixed to an underlying section of said diaper structure in the rear waist region to be entirely immoveable relative to the underlying section of the diaper structure.

11. The diaper according to claim 1, wherein each of said antislip elements comprises:

a first edge coinciding with a side edge of the respective side flap region of the rear waist region; and a second edge coinciding with an end edge of the rear waist region, wherein said end edge defines a partial circumferential edge of a waist opening when the tape fasteners are attached to the outer surface of the front waist region.

12. The diaper according to claim 11, wherein said antislip elements are permanently bonded to the outer surface of the diaper structure by adhesives applied on whole areas of the respective antislip elements.

13. The diaper according to claim 4, wherein said antislip elements are permanently bonded to the outer surface of the diaper structure by adhesives applied on whole areas of the respective antislip elements.

* * * * *